United States Patent
Basque et al.

(10) Patent No.: US 8,197,630 B2
(45) Date of Patent: Jun. 12, 2012

(54) LASER WELDING SYSTEM FOR SEALING OR CUTTING POLYMERIC SHEETS

(75) Inventors: Roland Basque, Brossard (CA); Alain Cournoyer, Québec (CA); Marc Levesque, St-Augustin-de-Desmaures (CA)

(73) Assignee: Glopak Inc., Montreal (CA)

( * ) Notice: Subject to any disclaimer, the term of this patent is extended or adjusted under 35 U.S.C. 154(b) by 0 days.

(21) Appl. No.: 11/583,058

(22) Filed: Oct. 19, 2006

(65) Prior Publication Data

US 2007/0034062 A1 Feb. 15, 2007

Related U.S. Application Data

(62) Division of application No. 10/722,131, filed on Nov. 26, 2003, now Pat. No. 7,344,671.

(51) Int. Cl.
| | |
|---|---|
| B65B 51/10 | (2006.01) |
| B65B 9/00 | (2006.01) |
| B29C 65/16 | (2006.01) |
| B29C 65/74 | (2006.01) |
| B29C 65/06 | (2006.01) |
| B65B 9/02 | (2006.01) |
| B65B 9/04 | (2006.01) |

(52) U.S. Cl. ............ 156/272.8; 156/73.5; 156/251; 156/264; 156/269; 53/450; 53/451

(58) Field of Classification Search .......... 156/272.8, 156/73.5, 250–272.2
See application file for complete search history.

(56) References Cited

U.S. PATENT DOCUMENTS

| | | | |
|---|---|---|---|
| 3,989,778 A | 11/1976 | Osborne | |
| 4,458,133 A * | 7/1984 | Macken | 219/121.67 |
| 4,776,904 A * | 10/1988 | Charlton et al. | 156/73.1 |
| 4,798,931 A * | 1/1989 | Hess, III | 219/121.64 |
| 4,924,062 A | 5/1990 | Zurcher | |
| 4,945,203 A * | 7/1990 | Soodak et al. | 219/121.64 |
| 5,173,583 A | 12/1992 | de Contencin et al. | |
| 5,502,292 A * | 3/1996 | Pernicka et al. | 219/121.64 |
| 5,595,670 A | 1/1997 | Mombo-Caristan | |
| 5,630,308 A | 5/1997 | Guckenberger | |
| 5,659,479 A | 8/1997 | Duley et al. | |

(Continued)

FOREIGN PATENT DOCUMENTS

DE 19832168 1/2000

(Continued)

OTHER PUBLICATIONS

"Lateral." Merriam-Webster Online Dictionary. 2009. Merriam-Webster Online. Jul. 27, 2009 <http://www.merriam-webster.com/dictionary/lateral>.*

(Continued)

*Primary Examiner* — Sonya Mazumdar
(74) *Attorney, Agent, or Firm* — Norton Rose Canada LLP

(57) ABSTRACT

A laser welding system for sealing or cutting polymeric sheets is described. The system comprises a laser source capable of delivering a laser beam. The laser beam is projected onto a region of the polymeric sheets where the sealing or cutting is to be performed. An optical device is provided to image the sealing or cutting as it is performed. An image analyser asserts the sealing or cutting quality. An integrated control means is provided to control the laser source, the projection of the laser beam, the optical device and the image analyser.

2 Claims, 10 Drawing Sheets

U.S. PATENT DOCUMENTS

| | | | |
|---|---|---|---|
| 5,701,725 | A | 12/1997 | Neri et al. |
| 6,103,050 | A | 8/2000 | Krueger |
| 6,237,308 | B1 | 5/2001 | Quintin et al. |
| 6,387,209 | B1 | 5/2002 | Nettesheim |
| 6,670,574 | B1 | 12/2003 | Bates et al. |
| 6,818,857 | B1 * | 11/2004 | Cho et al. ............ 219/121.64 |
| 7,214,173 | B2 * | 5/2007 | Barclay et al. ............ 493/213 |
| 7,344,671 | B2 * | 3/2008 | Basque et al. ............ 264/400 |
| 7,367,931 | B2 * | 5/2008 | Barclay et al. ............ 493/341 |
| 7,462,256 | B2 * | 12/2008 | Basque et al. ............ 156/379.6 |
| 7,750,269 | B2 * | 7/2010 | Barclay et al. ............ 219/121.67 |
| 2002/0008809 | A1 | 1/2002 | Babuka et al. |
| 2002/0074082 | A1 * | 6/2002 | Yu et al. ............ 156/256 |
| 2002/0144984 | A1 | 10/2002 | Mori et al. |

FOREIGN PATENT DOCUMENTS

| | | |
|---|---|---|
| EP | 0 472 850 A2 | 4/1992 |
| EP | 0 472 850 A3 | 4/1992 |
| WO | WO 98/16430 | 4/1998 |

OTHER PUBLICATIONS

English translation of DE19832168; Fuhrberg, Peter. Jan. 20, 2000.*

* cited by examiner

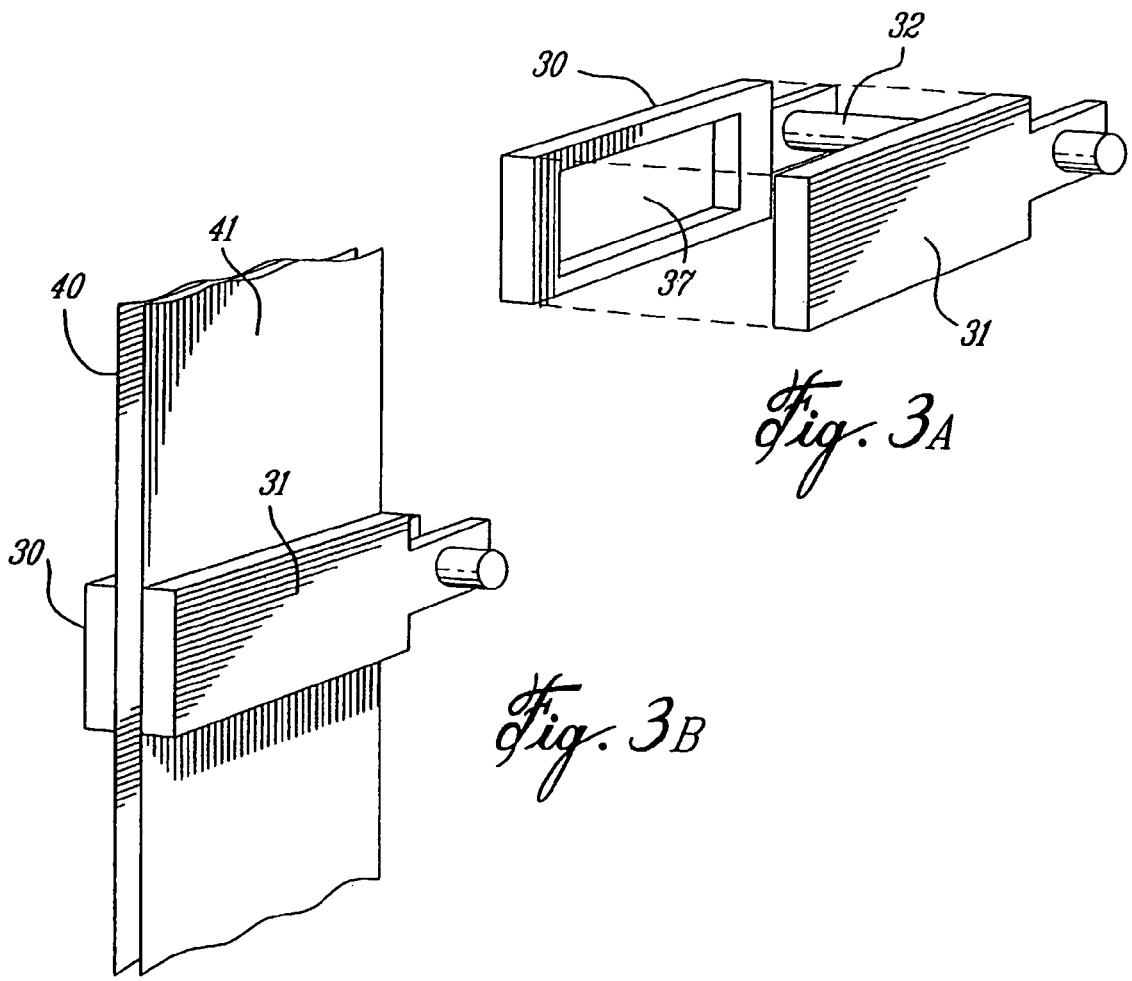
Fig. 3A
Fig. 3B
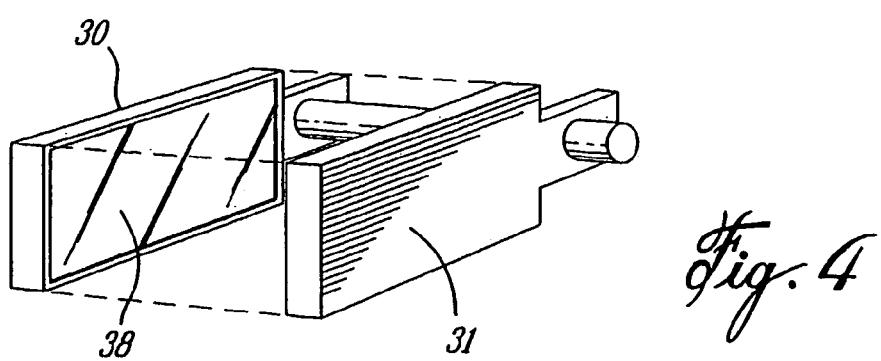
Fig. 4

LASER WELDING SYSTEM FOR SEALING OR CUTTING POLYMERIC SHEETS

CROSS-REFERENCE TO RELATED APPLICATION

The application is a divisional of application Ser. No. 10/722,131, filed Nov. 26, 2003 now U.S. Pat. No. 7,344,671.

FIELD OF THE INVENTION

The invention relates to a laser welding system for sealing or cutting polymeric sheets.

BACKGROUND OF THE INVENTION

In packaging industry, the welding and cutting of polymeric sheets is a very important issue. Polymeric materials are used to make all kinds of packages and in the case of food industry these packages can be for example pouches that contain liquid such as milk or sealed bags that contain solid food. For the food industry is it a requirement to have a packaging process that is reliable, of very high quality, and hygienic. Furthermore, the packaging process should be fast, efficient and easy to control.

In the industry of form/fill/seal packaging at high speed, conventional machines fall into two distinct categories, namely continuous and intermittent motion machines. In continuous motion machines, the packages are formed and sealed at a fixed speed and in intermittent motion machines, the package is momentarily immobilized at a cutting station for the time duration of the sealing process. Form/fill/seal packaging machines that are used to produce milk pouches are intermittent motion machines that can form/fill/seal milk pouches with typically a high rate of more than 1 liter per second. These machines use a heating system to seal and cut, in one operation step, the polymeric films therefore forming a bag or a pouch. Heating the polymeric films locally has the effect to weld the films together creating simultaneously two seals region separated by a region where the films are cut. The process must be well-controlled since too much heat can damage the integrity of the films whereas not enough heat will poorly weld the films.

In the industry of form/fill/seal packaging at high speed, the sealing systems that are generally in use utilize an electrical resistance wire that is heated by an electrical pulse. The heated wire is brought into contact with the films where the films are aimed to be sealed and cut, and the heat of the wire is transferred partially to the films therefore creating the seal. An example of this kind of machine can be found in U.S. Pat. No. 6,237,308 B1. Although this system allows for high speed packaging and is a well-mastered process, it has some drawbacks. The first drawback of this system is that the hot wire must be in contact (directly or indirectly via a disposable release sheet) with the films to transfer the heat to the films. This can lead to contamination problems and the hot wire and/or the release sheet must often be changed. The actual technique is also not a very efficient process since the film area that is heated via this process is much larger than what is really needed to make the seal. Finally, since the hot wire is located in a mechanical clamp that brings the films into contact, it is subject to mechanical vibrations that can affect the seal quality.

The use of lasers to seal and cut polymeric films in a continuous sealing apparatus is known from U.S. Pat. No. 6,207,925 B1. Three laser beams are controlled to perform the transverse seal-cut-seal action between two contiguous packages. Each laser is devoted to either seal or cut the films. Because of the continuous motion of the films, the time for the laser beams to perform the cut and seal is extended substantially to the whole package cycle. The teachings of U.S. Pat. No. 6,207,925 B1 cannot be readily adapted for use with intermittent motion form/fill/seal machines and the spot beam precision control in the case of continuous motion machines remains costly.

Therefore there is a need for a method and an apparatus for improving the sealing and cutting process of a high speed packaging machine, in order to increase the efficiency of the process, to reduce the mechanical contact between the heating source and the films, and to increase the overall lifetime of the machine components.

SUMMARY OF THE INVENTION

Accordingly, the object of the present invention is to provide a method of sealing and cutting optically polymeric films for packaging machines based on an optimized optical system using a laser or several lasers and a special optical clamp. The present invention can be applied to any polymeric sheets or films that require welding or cutting. The method allows for a more efficient optical sealing and cutting process in comparison with previous methods found in the prior art.

According to one aspect, there is provided a laser welding system for sealing or cutting polymeric sheets of a given width along a seal/cut length, the system comprising: a laser source delivering a laser beam having a varying intensity profile; and an optical device to project the laser beam as a single laser beam contacting a region of said polymeric sheets as a beam of elongated shape where said sealing or cutting is to be performed, said optical device adapted to shape the intensity profile of the single laser beam with respect to a volume of the region of said polymeric sheets, the intensity profile of the single laser beam having said elongated shape along the seal/cut length that is longer than said given width of said sheets, the intensity profile of the single laser beam projected on the region comprising a distributed intensity level along a perpendicular direction to said seal/cut length, the distributed single laser beam providing a central portion comprising a first intensity level to cut along said seal/cut length and lateral portions on said perpendicular direction comprising a second intensity level to seal along said seal/cut length, where the first intensity level is higher than the second intensity level, for the purpose of simultaneously obtaining, in one exposure step with the single laser beam, two sealed regions separated by a cut region in said volume, the two sealed regions each defining a portion of the volume where the films are sealed together, and the cut region defining another portion of the volume where the films are cut.

One feature of the present invention is to provide a method of sealing and cutting optically polymeric sheets or films with at least one laser beam having a shaped intensity profile for the purpose of obtaining in one exposition step a seal/cut/seal operation. The method comprises: shaping the at least one laser beam intensity profile by using an optical device to provide the desired intensity profile; superposing and bringing into contact at least two of said films together; and exposing an area of the films, the area being a seal-cut-seal volume, to the said desired intensity profile for the purpose of obtaining in one exposition step two sealed regions where the films are sealed together separated by a cut region where the films have been cut.

It is another feature of this invention to further improve the efficiency of the sealing and cutting process by having more of the laser beam intensity absorbed by the films, the method comprising: superposing and bringing into contact at least two polymeric films together; exposing an area of the films, the area corresponding to a sealing volume, to at least one laser beam, providing an incident laser intensity, for the purpose of sealing or cutting the films; increasing an intensity of the laser beam in the sealing volume by re-injecting partly or totally the laser beam intensity that has not been absorbed by the films back to the films by using at least one reflective device, therefore improving the efficiency of the sealing or cutting method by having more light intensity of said incident laser intensity absorbed by the films.

It is another feature of the present invention to provide an optical sealing clamp to optically seal or cut polymeric sheets or films with at least one laser beam, the clamp comprising: two jaws wherein at least one of said jaws can be moved to allow a closing and an opening of the clamp; one of said jaws, being a contact jaw, to bring the films into contact; the other jaw, being an optical jaw, having an optical window to let laser beams pass through it and wherein said window is wide enough to allow to optically seal or cut the whole width of said films; and support means to interconnect said jaws and to allow a controlled opening and closing of the clamp.

It is a further aspect of the above-described clamp to provide for an increase of the laser beam intensity in the films by having said contact jaw surface reflecting partially or totally the laser beam intensity that has not been absorbed by the films back to the films, therefore increasing the sealing and cutting process efficiency.

It is a further aspect of the above-described clamp to provide for an additional increase of the laser beam intensity in the films by having said optical jaw surface reflecting partially or totally the laser beam intensity that has not been absorbed by the films back to the films, therefore increasing even more the sealing and cutting process efficiency.

It is a further aspect of the above-described clamp to provide for an additional increase of the laser beam intensity in the films by having the surface of the jaws that are exposed to the unabsorbed laser intensity by the films profiled to allow for three back and forth reflections from one jaw to the other, allowing therefore for four passes of laser beam into the films.

It is another feature of the present invention to provide a method of monitoring the sealing and cutting process by optically imaging the seal and cut quality through the window of the clamp while the optical sealing and cutting process is being performed.

According to a still further broad aspect of the present invention there is provided two packaging methods that offer an improved sealing and cutting efficiency and that overcome or reduce some drawbacks of the prior art due to the direct contact of the heating source with the films, such as packages contamination and the short life-time of the sealing elements. Both methods are using at least one optical clamp the characteristics of which have been described above.

The first packaging method is a method of forming, sealing and cutting optically, and filling a pouch with a liquid at high speed. The method comprises: providing a vertical tube, made of polymeric film, that is partially or totally filled with a liquid, or that is being filled with a liquid; flattening a filled section of said tube for a determined time interval using an optical sealing clamp for subsequent optical sealing and cutting of said section of said tube; exposing said section of said tube to at least one laser beam intensity, for a time exposure interval τ, to heat in a controlled manner said section of said tube, said intensity being shaped to obtain a desired intensity profile and to provide a corresponding absorbed intensity profile in said section of said tube; providing a desired heat amount to said section of said tube by optimizing a combination of said absorbed intensity profile, said time exposure interval, and by heating if required said optical sealing clamp; obtaining as a result two seals across said section of said tube and simultaneously severing said tube between the seals, to form a top seal for a filled pouch that is separated form said tube and a bottom seal for said vertical tube.

The second packaging method is a method of sealing or sealing-and-cutting packages made with polymeric sheets or films using at least one laser source and at least one optical sealing clamp, the method comprising the steps of: providing a partially or completely formed package that is partially or completely filled with its content or being filled with its content; superposing and bringing into contact an inner wall of a section of said package for subsequent sealing by means of an optical sealing clamp; exposing said section of said package to at least one laser beam intensity, for a time exposure interval τ, to heat in a controlled manner said section of said package, said intensity being shaped to obtain a desired intensity profile and to provide a corresponding absorbed intensity profile in said section of said package; providing a desired heat amount to said section of said package in order to perform either a sealing operation or a sealing-and-cutting operation, by optimizing a combination of said absorbed intensity profile, said time exposure interval, and by heating if required said optical sealing clamp; obtaining as a result in the case of the sealing operation, a seal across said section of said package, and in the case of the sealing-and-cutting operation, two seals across said section of said package and simultaneously a cut region between the two seals where the package is cut.

The packaging methods described above can further provide for a monitoring of the sealing or sealing-and-cutting operation by inspecting, using an optical detection assembly, the package being sealed through the optical window of the optical sealing clamp, while the sealing or sealing-and-cutting operation is being performed.

The packaging methods described above can further comprise the partial or total re-injection of the laser beam intensity that has not been absorbed in step iii) by means of the reflective property of the optical sealing clamp, in order to enhance in a controlled manner heat in the section of the films that are to be sealed and cut.

BRIEF DESCRIPTION OF THE DRAWINGS

The preferred embodiments of the present invention will now be described with reference to the accompanying drawings in which:

FIG. 3A and FIG. 3B are showing a clamp in opened position (3A) and in closed position (3B). One of the jaw has an aperture;

FIG. 4 is showing a clamp with a ZnSe window;

It will be noted that throughout the appended drawings, like features are identified by like reference numerals.

DETAILED DESCRIPTION OF THE PREFERRED EMBODIMENT

Figure 1:
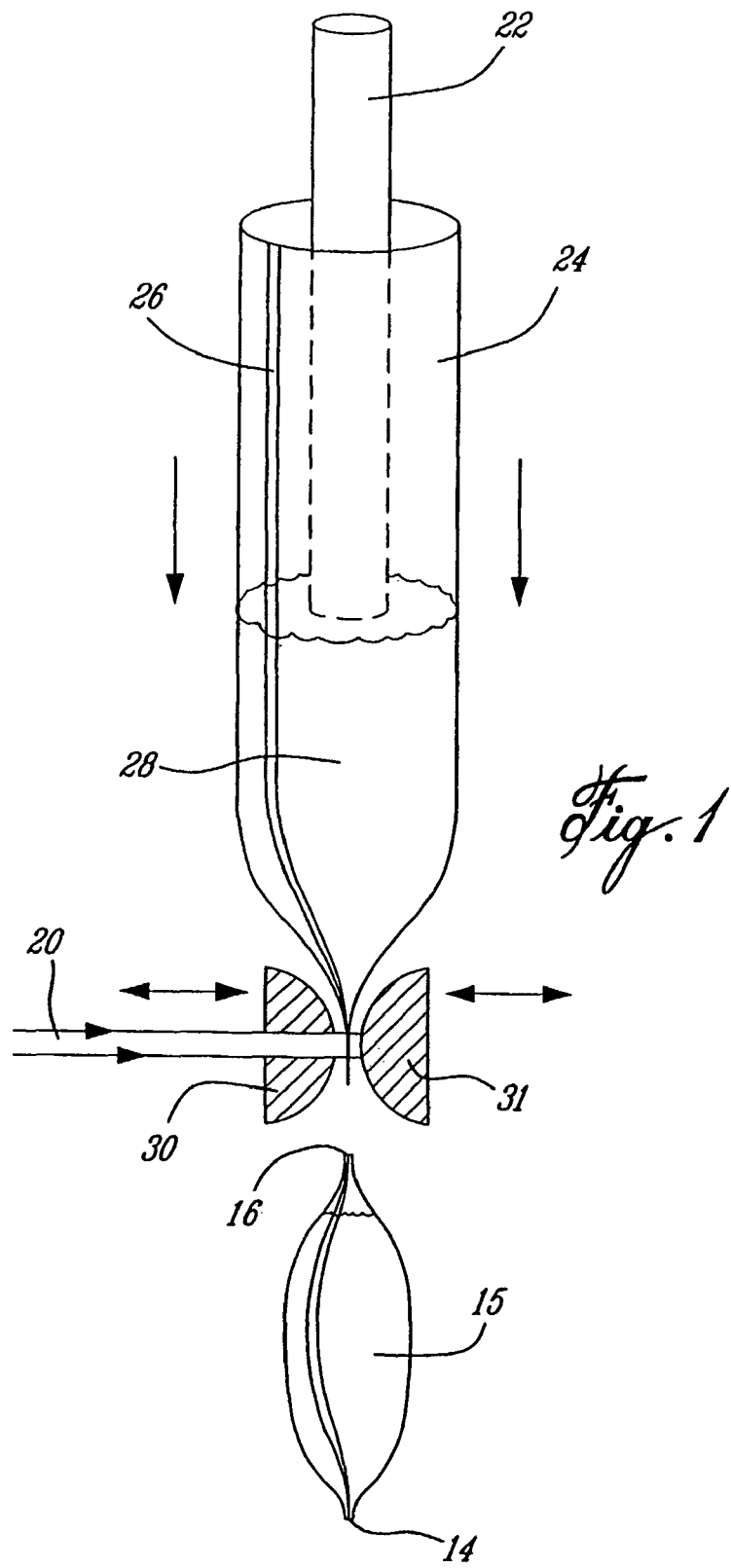
FIG. 1 is a drawing showing a vertical machine that is forming pouches, filling them with a liquid and sealing them.

In this detailed description of the preferred embodiment we will focus on food industry form/fill/seal intermittent machines (FFS) where the package is momentarily immobilized at a cutting station for the time duration of the sealing process. FIG. 1 is a schematic illustration of the preferred embodiment of this invention where a vertical form/fill/seal machine (VFFS) is shown. VFFS machines are commonly used to manufacture milk pouches. In this type of machine, a tube 24 made from a polymeric flexible film is continuously filled with a liquid 28 by a liquid delivering device 22. The tube 24 has been previously formed (not shown on this figure) from a roll of a polymeric flexible film that has been vertically sealed 26 using a vertical sealer clamp. A horizontal optical clamp having two jaws 30, 31 repeatedly opening and closing, allows for the production of filled pouches 15 at a rate of about 1 pouch per second. While being closed on the tube, the clamp momentarily immobilized it for the time duration of the sealing process, after which it reopened to leave passage to another length of tube.

The present invention proposes a method and a special optical clamp to improve the efficiency of the optical sealing and cutting process of flexible films in the context of high speed intermittent machines. It also presents a way to seal an cut flexible polymeric films with indirect contact between the heating system source and the films therefore reducing contamination problems. As shown in FIG. 1 a laser beam 20 passes through the first jaw 30, referred to as an optical jaw, and impinges on the two layers of the tube that have been previously brought into contact by closing the jaws 30, 31 of the clamp. The laser beam is absorbed by the films partially or totally in a volume referred to as the sealing volume and the absorbed energy heats the films causing the sealing process between the films. With enough absorbed energy in the sealing volume, the films will be cut. By controlling the amount of absorbed energy by the films it is possible in one operation to seal and cut the flexible films. It is a characteristic of the present invention, as it will be described later in this disclosure, to present a method to control and optimize the absorbed energy by the films.

Typically the films have a thickness less than 100 microns and they contain a large proportion of polyethylene. In the manufacturing of milk pouches, the transverse seals 14, 16 have a length of about 6 inches. The optical clamp therefore needs to have a length of at least 6 inches to seal a pouch.

Figure 2:
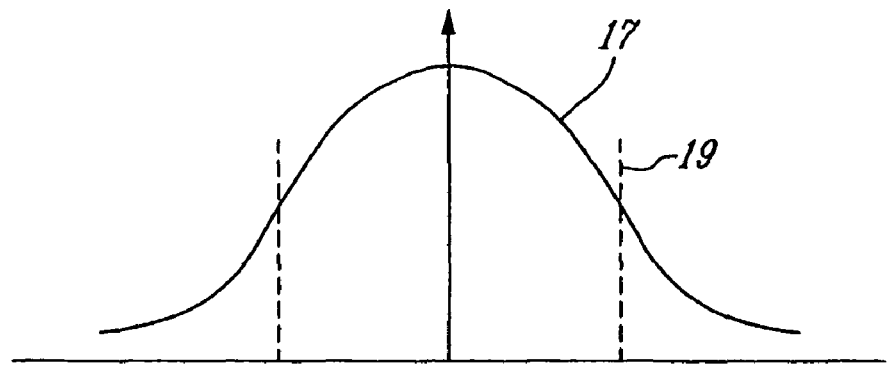
FIG. 2 is a graph showing the intensity distribution of the laser spot at the level of the films along the seal length (y axis) and in the perpendicular direction (x axis)
Figure 2:
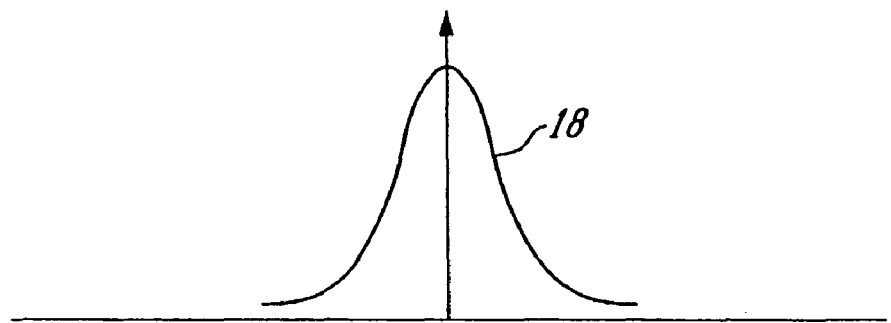

The laser used in this preferred embodiment is a $CO_2$ laser 50 emitting at a wavelength of 10.6 microns less than 100 watts of power. It will be understood by a person skilled in the art that another type of laser or a $CO_2$ laser emitting at another wavelength could as well be used. The $CO_2$ laser beam is shaped in order to get the desired intensity profile where the films have to be sealed or sealed and cut. The $CO_2$ laser beam 20 can by either focused to a spot of about 1 mm of diameter 53 at the level of the films or it can be shaped, using an appropriate optical device, in an elongated spot 58 that can cover the whole width (6 inches) of the films. In the first case, shown in FIG. 12, the laser beam is scanned over the films width sealing in about half a second the whole width of the films. In the second case, shown in FIG. 11, the laser beam shaped in a horizontally elongated spot impinges the films for about half a second. In both cases the time exposition of the films can be controlled by a switch 57 that can interrupt the laser beam. FIG. 2 illustrates the intensity profile of the laser spot on the surface of the films in the case of an elongated spot 58: along the seal length 17 and in the perpendicular direction 18. The hatched lines 19 on the graph are showing the films width extremities. The elongated beam is generally longer than the film width so that the incoming intensity is large enough to seal the films and to insure that the intensity along the sealing volume is not below an insufficient value. In the case where the laser spot is circular the distribution is the same in both axis and is similar to the distribution 18. By controlling the beam intensity profile by appropriate shaping of the beam, it is possible to control the absorbed energy distribution in the films. In particular an appropriate shaping on the laser beam will provide in one operation two seals regions separated by a region where the films are cut. This control of the absorbed energy distribution is a characteristic of the present invention.

The intensity absorbed by the films will depend on the impinging intensity and on the absorption capacity of the films. The type of films that are used to make milk pouches will typically absorb only about 10% of the laser intensity because of their thickness of only about 100 microns. Thicker films would of course absorb more and films having a special absorbing layer could also absorb a bigger portion of the impinging laser beam. However it is a feature of the present invention to provide a way to increase the absorbed light by the films by allowing for multi passes of the laser beam in the films as it will be discussed later in this disclosure.

The sealing and cutting process depends on many factors such as the amount of laser intensity that is absorbed, the distribution of the energy absorption within the films, the time exposition of the films, and on thermal characteristics of the films such as the thermal conductivity of the films. It was found in this preferred embodiment that high quality seals were obtained by exposing the films to a total energy of less than 100 Joules per cm. That corresponds in the case of a laser beam shaped into an elongated spot to an exposition time of less than a second to produce two high quality seals along the whole width of the films that are separated be a region where the films have been cut.

Figure 5:
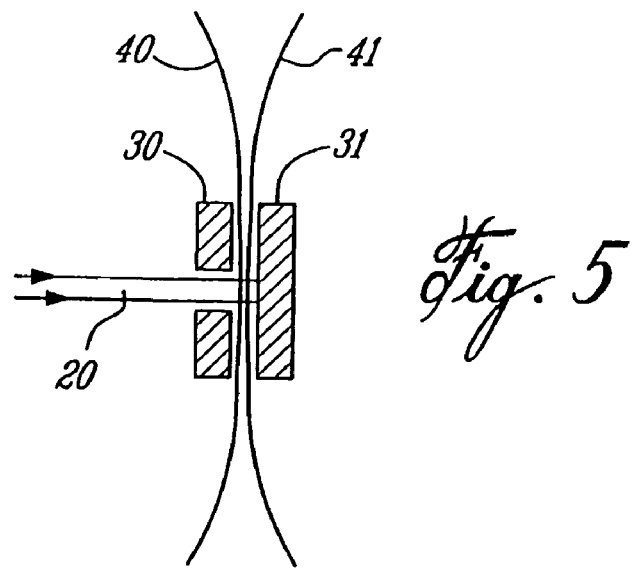
FIG. 5 is a side view of a clamp in a closed position. The clamp is bringing into contact two flexible polymeric films and an incoming laser beam is sealing and cutting the films.

We will now describe in more details several optical clamp designs that can be used in this invention to seal and cut the films. FIG. 3A illustrates the main parts of the clamp: the optical jaw 30 and the other jaw 31 can be moved via a mechanism 32 to a closed position as shown in FIG. 3B in order to bring in contact the two films 40 and 41 prior to the sealing process. The optical jaw is characterized by the fact that is has a window wide enough to allow sealing in a unique operation the whole width of the film. The laser beam 20 passes through that window to impinge on the films as shown in FIG. 5. The window can be an aperture 37 in a metallic structure has shown on FIG. 3A, it can also be an aperture covered by an optical material, it can be made completely of a transparent material 38, or it could be a mounting plate for a series of miniature lasers. The other jaw 31 can allow for reflecting back to the films the laser intensity that have not been absorbed in the first laser pass, increasing therefore the amount of laser light intensity available to the films.

Figure 6:
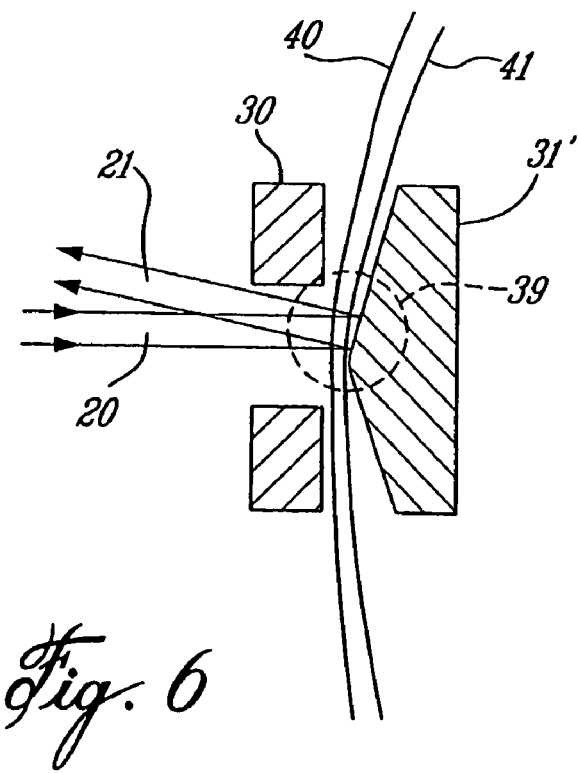
FIG. 6 is a side view of a clamp with one jaw profiled to apply a tension on the films and reflect partially or totally the light that was not absorbed by the films back to the films.

When the jaw 31 is meant to reflect partially or totally the incoming unabsorbed laser light, its surface can be a metallic polished. The jaw can also be profiled 31' as shown in FIG. 6 to apply a tension on the films while bringing them into contact. Tension needs to be controlled in the case of thin plastic films to avoid a stretching and thinning of the films before a seal or cut is effected.

Figures 7A, 7E:
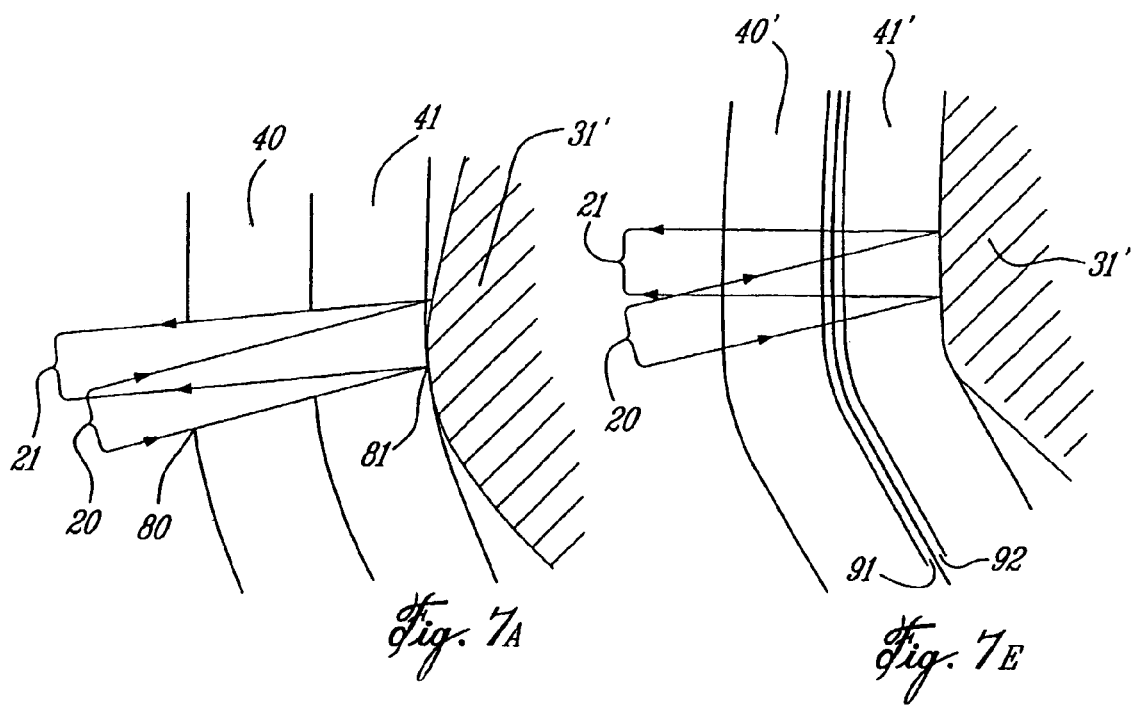
FIG. 7A is a close-up illustration of the sealing region where the incident laser beam is propagating across the two films and is reflected back by the jaw to the films. The evolution of the beam intensity along the sealing volume is shown below in the forward direction FIG. 7B and the backward direction (FIG. 7C).
FIGS. 7E, 7F,7G, and 7H shows the same information in the case where the films are composed of one slightly absorbing layer and one strongly absorbing layer.
Figures 7B, 7F:
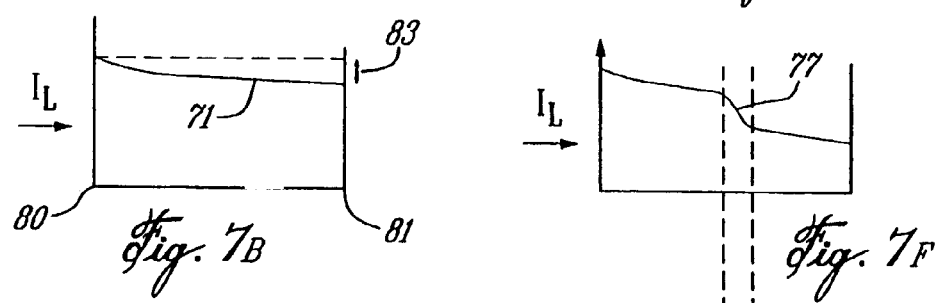
Figures 7C, 7G:
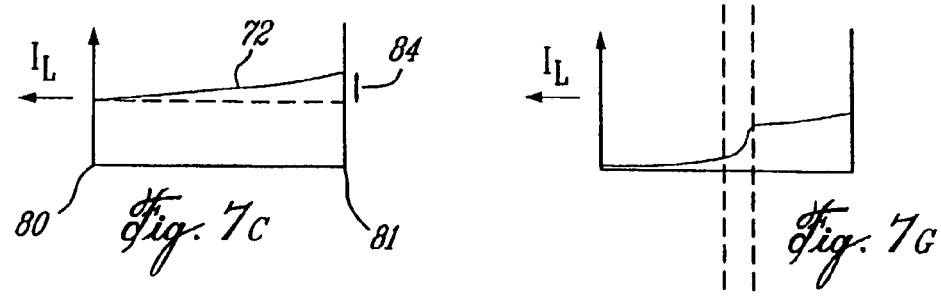
Figures 7D, 7H:
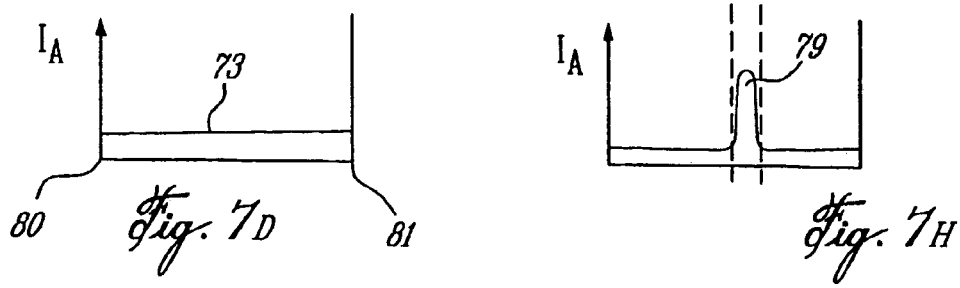
FIG. 7D shows the absorbed beam intensity.

FIG. 7A is a close-up of the films sealing region 39 showing the incident laser beam 20 passing through the two films, the unabsorbed laser intensity is then hitting the contact jaw 31' that has been profiled to reflect it back 21 to the films. Since the films are absorbing a small portion of the laser intensity, this technique can allow ideally to roughly doubling the laser light in the sealing volume providing that the jaw 31' has a high reflectivity coefficient. The three following graphs-show how the laser intensity changes along its propagation in the films due to its absorption by the films. FIG. 7B is showing how the laser intensity is reduced during its propagation through the films in the first pass 71 and FIG. 7C is showing how the laser intensity is reduced on its way back 72. After one pass, the laser intensity has been reduced by an amount 83 and in a second pass by an amount 84. That intensity has been absorbed 73 by the films as shown on FIG. 7D and is roughly twice the absorbed laser intensity of only one laser pass.

FIGS. 7E, 7F, 7G, and 7H show what happen when the films have a high absorption layer 91 or 92. Because of the layers high absorption capacity, the laser intensity is highly absorbed 79 at their level resulting in a non-uniform absorption and therefore to a non-uniform and localized heating of the films. In some cases a localized heating of the films may be a better approach than a uniform heating of the films.

Figure 8A:
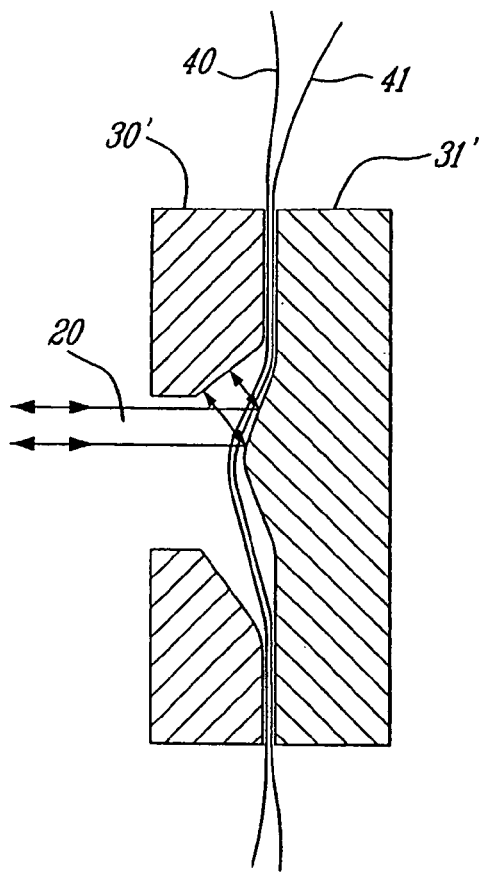
FIG. 8A is a side view illustration of a clamp with both jaws profiles to allow for 4 passes of the laser light in the films.
Figure 8B:
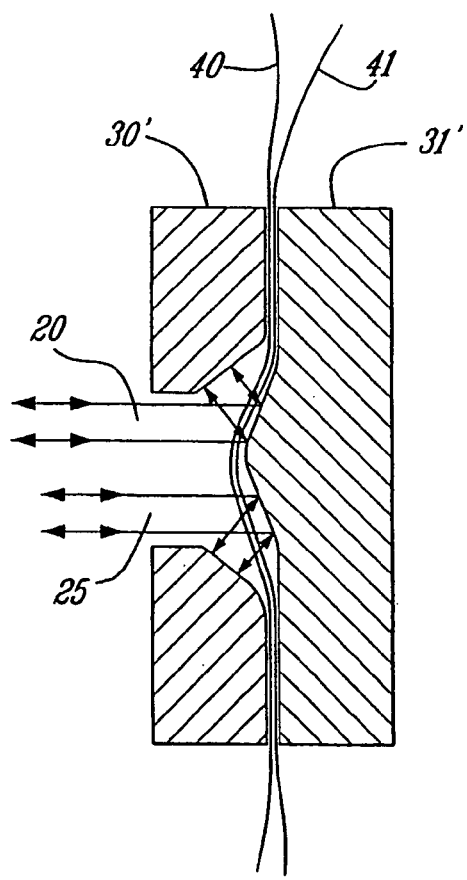
FIG. 8B shows the same clamp being used with two laser beams.
Figure 10:
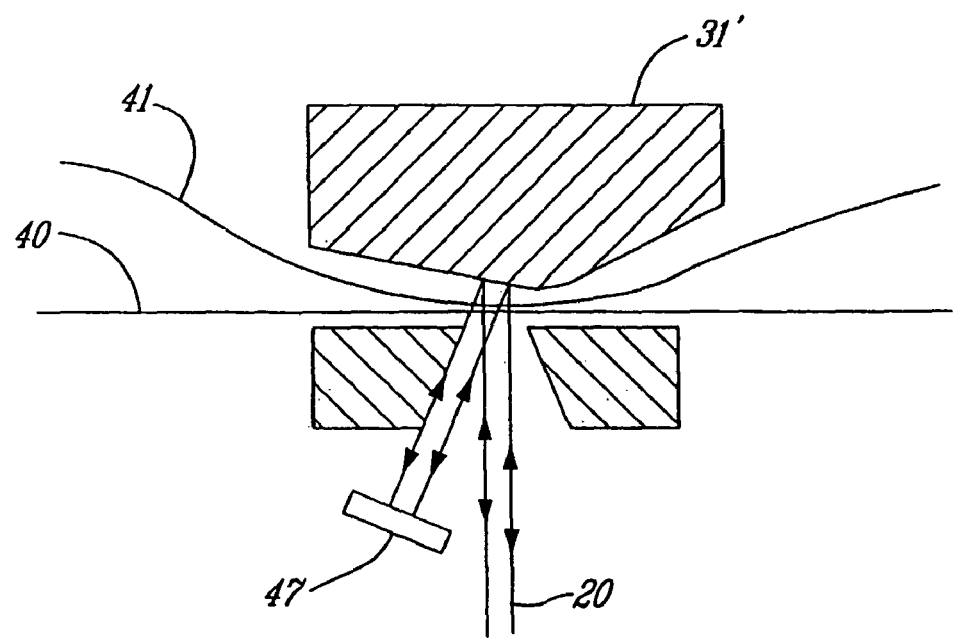
FIG. 10 is a side view of a clamp where a mirror attached to it reflects back to the film the unabsorbed light.

The optical clamp can also provide four passes of the laser beam 20 in the films. FIGS. 8A and 8B illustrate such a clamp. The optical jaw has a window that is profiled in order to reflect back to the films the unabsorbed laser light after the second laser pass. This embodiment provides an even higher efficiency of laser sealing and cutting of flexible polymeric films. Other profiles of the clamp's jaws can allow for multi-pass of the laser light through the films as it will be apparent to those skilled in the art. It will also be understood that the reflection process of the unabsorbed laser beam intensity can be provided by the use of reflection devices that are located externally of the window such as shown in FIG. 10 where a mirror 47 is used to reflect the unabsorbed light back to the films.

Figure 9:
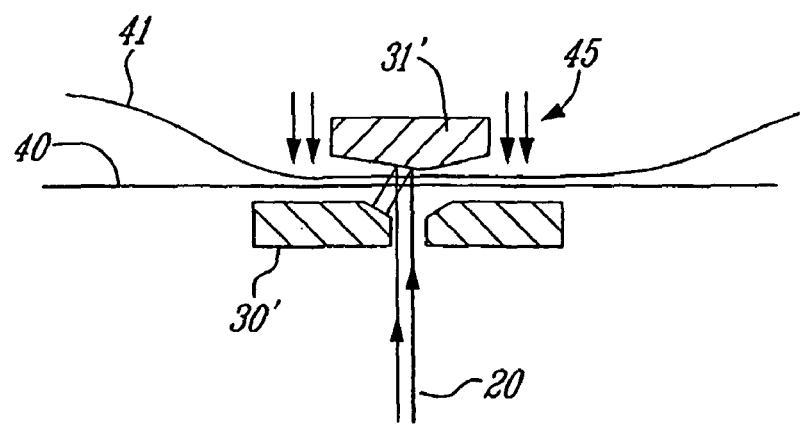
FIG. 9 shows a side view of a clamp using air streams to bring into contact the films.

The optical clamp can also be used in combination with an air system to bring into contact the films to be sealed. This is illustrated in FIG. 9 where pulsed air streams 45 are maintaining the films in contact while being sealed by the laser.

The optical clamp can naturally be used with more than one laser as illustrated in FIG. 8B where two beams, 20 and 25, are simultaneously sealing and cutting the films. This embodiment can add flexibility to the packaging system by enabling to control separately the sealing and the cutting process for example.

The clamp can furthermore be heated to help the sealing and cutting process by providing a pre-heating of the films.

All the above possible optical clamps designs provide a more efficient way to seal and cut flexible polymeric films or sheets as well as allowing for indirect contact between the heating system source (laser source) and the films therefore reducing contamination problems.

Figure 14:
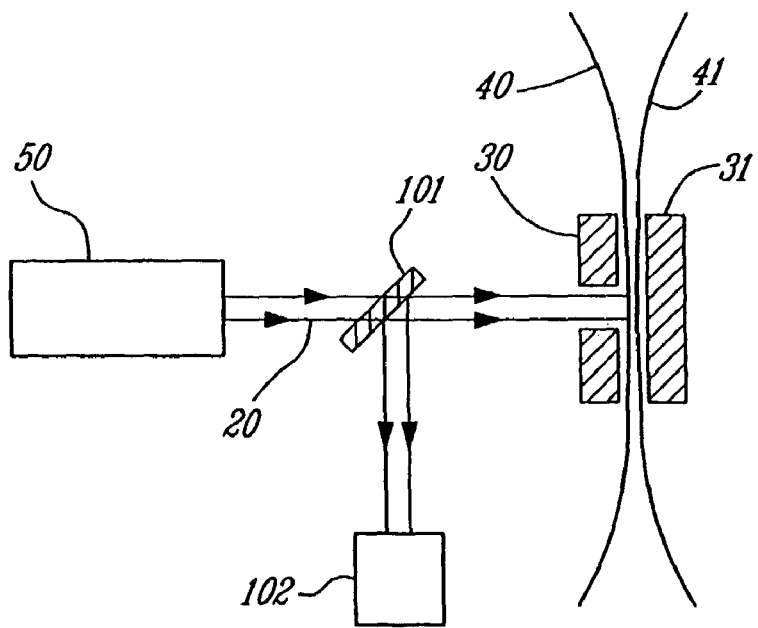
FIG. 14 is a schematic illustration of an optical set-up to monitor the sealing process of two films.

Furthermore all the above clamp designs allow inspecting the quality of the sealing or cutting operation of the films while these operations are being performed. An example of a possible way to realize this quality monitoring is shown in FIG. 14, where a beam splitter 101 has been inserted between the laser 50 and the optical jaw 30, enabling to optically inspect the seal quality as it is being performed. An optical assembly 102 comprising a detector and focusing optics, a camera for example, is used to detect light intensity emitted by the films being sealed. Therefore some optical signature of the seal can be obtained and be used to control the sealing and cutting process.

Figure 11:
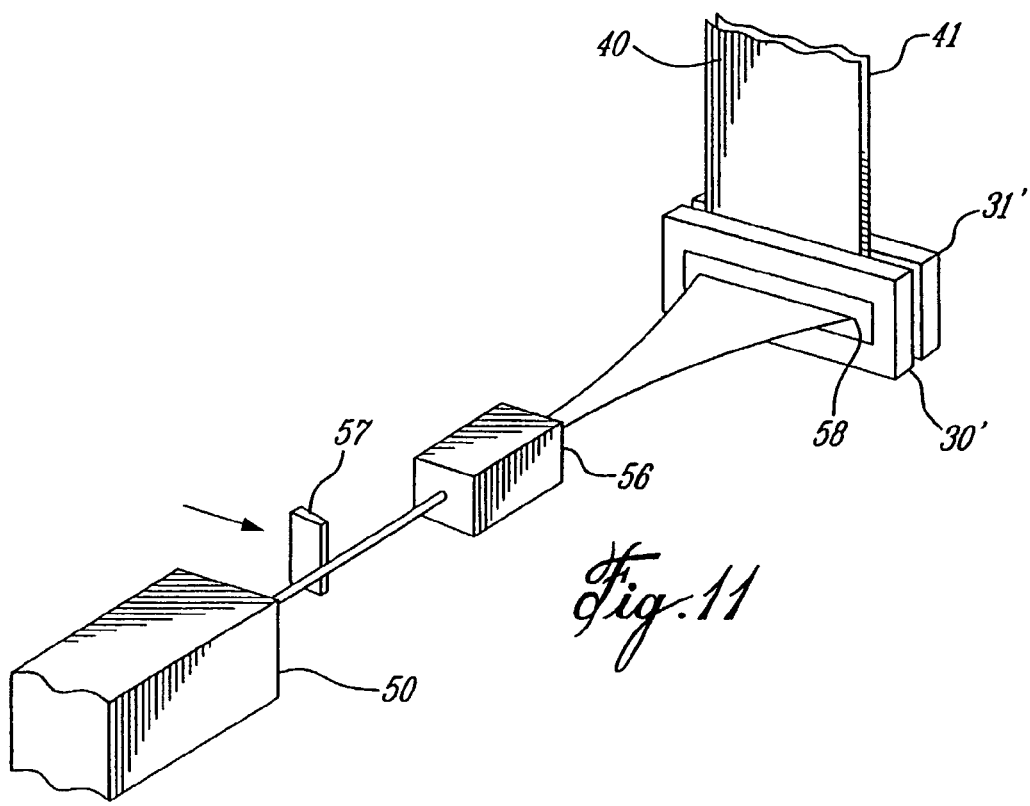
FIG. 11 is a schematic illustration of the optical system used to provide a laser elongated spot on the films to allow for the sealing and cutting of the whole films width.
Figure 12:
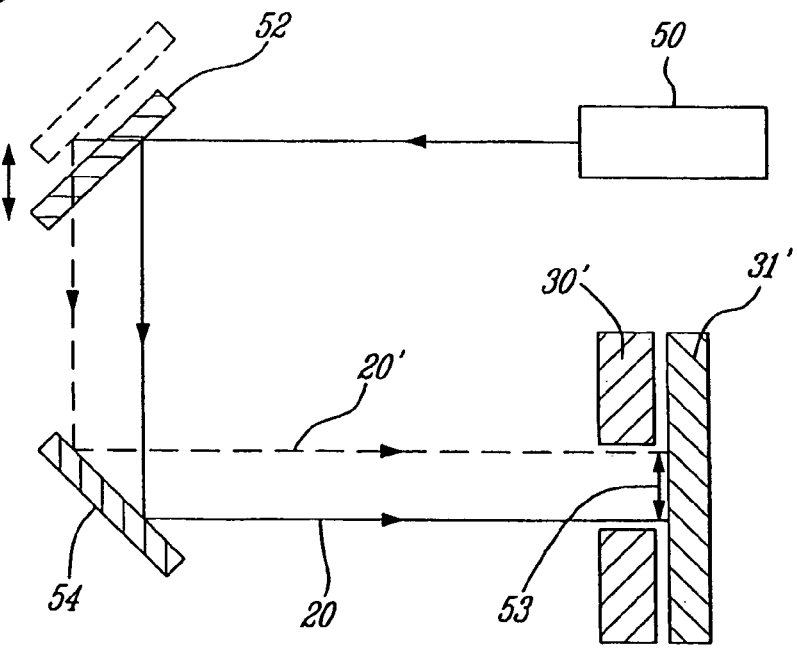
FIG. 12 is a schematic illustration (top view) of the laser beam scanning system that allows to seal and cut the whole width of the films. The clamp is shown from the top.

The clamps can allow for a scanning of a laser beam along the sealing volume or for an exposition of the films by an elongated laser beam. In both cases, the clamps allow sealing the whole film width via its window. FIG. 12 illustrates a possible scanning laser system where the laser beam 20 can be scanned along the sealing volume 53 by moving the mirror 52. FIG. 11 illustrates the case where the whole width of the film is exposed to an elongated laser spot 58. The laser beam intensity is shaped by an optical device 56 in this elongated spot. It will be appreciated by someone skilled in the art that other form of laser spots can as well be generated and used to seal and cut the films. Special laser beam shapes can be obtained with appropriate optical devices. The laser beam intensity profile is optimized via this shaping method to seal-cut-seal in one exposure step the films and therefore obtain two sealed regions where the films are sealed together separated by a cut region where the films have been cut.

Figure 13A:
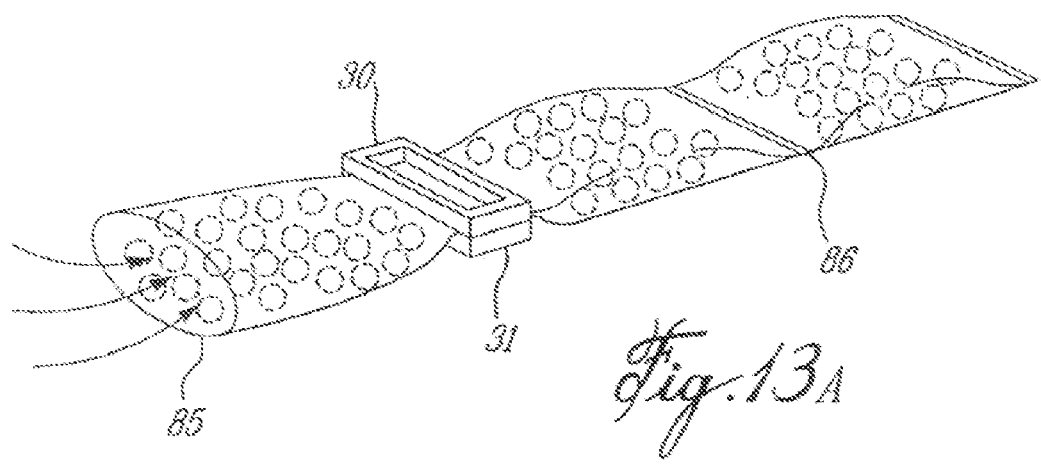
FIGS. 13A, 13B, and 13C are schematic illustrations of other packaging systems.
Figure 13B:
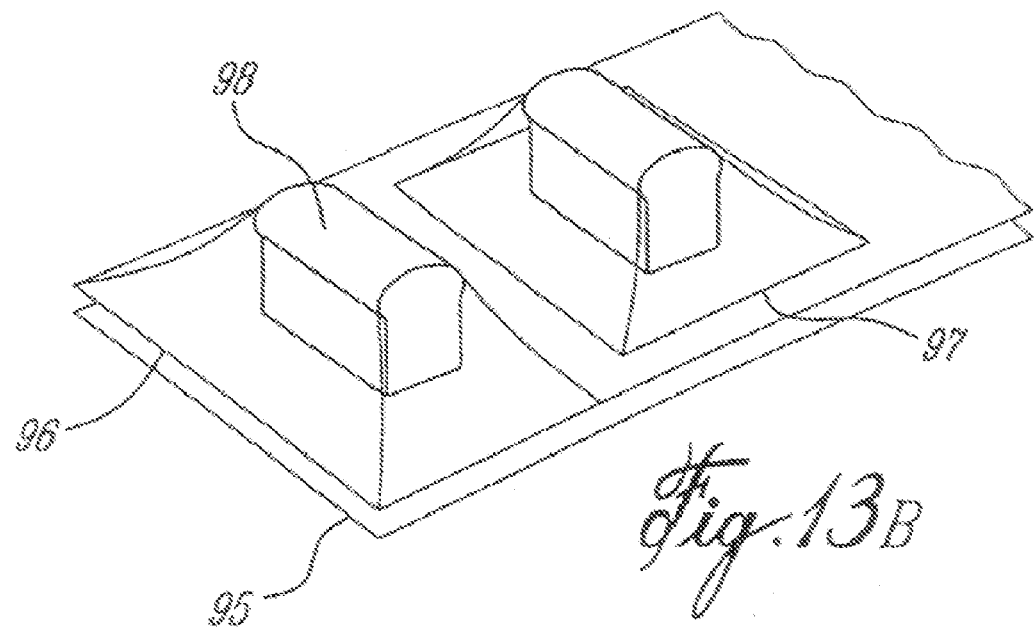
Figure 13C:
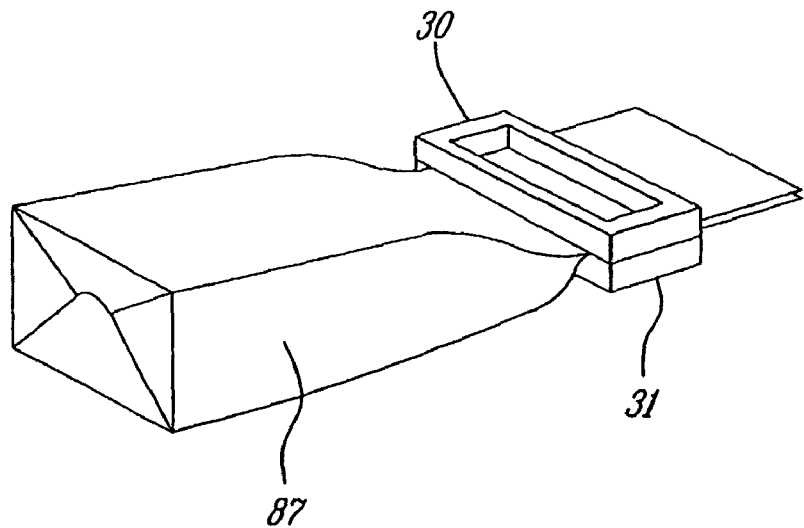

The present invention can as well be implemented for other packaging systems. FIGS. 13A, 13B, and 13C are examples of other embodiments of this invention where an optical clamp in combination with a laser is used to seal a package. FIG. 13A shows a tube filled 85 with solid food that has been sealed 86 by an optical clamp 30, 31. FIG. 13C is showing a bag being sealed by a laser using an optical clamp. FIG. 13B illustrates an aliment that has been in a first step placed on a polymeric sheet 95 and then covered by another polymeric sheet 96. The films 95, 96 are sealed and cut with a laser and using an optical clamp, a package is formed.

It will be understood that numerous modifications thereto will appear to those skilled in the art. Accordingly, the above description and accompanying drawings should be taken as illustrative of the invention and not in a limiting sense. It will further be understood that it is intended to cover any variations, uses, or adaptations of the invention following, in general, the principles of the invention and including such departures from the present disclosure as come within known or customary practice within the art to which the invention pertains and as may be applied to the essential features herein before set forth, and as follows in the scope of the appended claims.

We claim:

1. A laser welding system for sealing or cutting polymeric sheets of a given width along a seal/cut length, the system comprising:

a fixed laser source delivering a laser beam having a varying intensity profile; and a fixed optical device to project the laser beam as a single laser beam contacting a region of said polymeric sheets where said sealing or cutting is to be performed as a fixed beam of elongated shape, the elongated shape having a longitudinal dimension longer than said given width of said sheets and having a width dimension perpendicular to said longitudinal dimension, said optical device adapted to shape the intensity profile of the single laser beam with respect to a volume of the region of said polymeric sheets, the intensity profile comprising a distributed intensity level along the width dimension perpendicular to said seal/cut length, the distributed single laser beam providing a central portion comprising a first intensity level to cut along said seal/cut length and lateral portions on said perpendicular direction comprising a second intensity level to seal along said seal/cut length, where the first intensity level is higher than the second intensity level, for the purpose of simultaneously obtaining, in one exposure step with the single laser beam, two sealed regions separated by a cut region in said volume, the two sealed regions each defining a portion of the volume where the films are sealed together, and the cut region defining another portion of the volume where the films are cut.

2. The laser welding system as claimed in claim 1, further comprising:

a camera to image the sealing or cutting as it is performed;

an image analyzer for asserting a sealing or cutting quality; and an integrated control means to control said laser source, said optical device, said camera and said image analyzer.

* * * * *